United States Patent
Wright et al.

(10) Patent No.: US 6,995,287 B2
(45) Date of Patent: Feb. 7, 2006

(54) SYNTHESIS OF VINYLSULFONES

(75) Inventors: Charles W. Wright, Fairport, NY (US); James J. Seifert, Hilton, NY (US); Stephen A. Godleski, Fairport, NY (US); Marshall L. Vandewalle, Alton, NY (US); Paul P. Spara, Fairport, NY (US)

(73) Assignee: Eastman Kodak Company, Rochester, NY (US)

( * ) Notice: Subject to any disclaimer, the term of this patent is extended or adjusted under 35 U.S.C. 154(b) by 0 days.

(21) Appl. No.: 11/071,710

(22) Filed: Mar. 3, 2005

(65) Prior Publication Data

US 2005/0148798 A1     Jul. 7, 2005

Related U.S. Application Data

(63) Continuation of application No. 10/712,223, filed on Nov. 13, 2003, now abandoned.

(51) Int. Cl.
*C07C 321/00* (2006.01)
*C07C 323/00* (2006.01)
*C07C 381/00* (2006.01)

(52) U.S. Cl. .......................................... 568/22; 568/28

(58) Field of Classification Search .................. 568/22, 568/28
See application file for complete search history.

(56) References Cited

U.S. PATENT DOCUMENTS 4,171,976 A * 10/1979 Burness et al. ............. 430/621
4,173,481 A    11/1979 Sera et al.

FOREIGN PATENT DOCUMENTS

| EP | 0 640 589 A1 | * | 3/1995 |
| EP | 0 640 589 |   | 3/1997 |
| JP | 2000072741 | * | 3/2000 |

OTHER PUBLICATIONS

CA:132:194112 abs of JP2000072741 Mar. 2000.
CA:102:119627 abs of JP59210015 Nov. 1984.

* cited by examiner

*Primary Examiner*—Johann Richter
*Assistant Examiner*—Chukwuma Nwaonicha
(74) *Attorney, Agent, or Firm*—Arthur E. Kluegel

(57) ABSTRACT

Disclosed is a process comprising reacting a primary alcohol sulfone with a reducing agent and a halogenating agent in the presence of an amide compound present in an amount of less than 1 part amide per part of primary alcohol sulfone to form a vinylsulfone.

13 Claims, No Drawings

SYNTHESIS OF VINYLSULFONES

CROSS-REFERENCE TO RELATED APPLICATION

This is a continuation of application Ser. No. 10/712,223 filed Nov. 13, 2003, now abandoned.

FIELD OF THE INVENTION

This invention relates to improvements in the process for synthesizing compounds containing two or more vinyl sulfone groups through non-isolation of the intermediate step materials.

BACKGROUND OF THE INVENTION

Hydrophobic colloidal gels such as photographic gelatin emulsion are made more stable or "hardened" by the addition of compounds that cross-link the protein chains of the gelatin. Chemical compounds that contain two or more vinyl sulfone groups are well known cross-linking agents and are widely used in the photographic industry. These materials are generally manufactured in a step-wise manner from isolated halo ethyl sulfone compounds using organic or inorganic bases.

These known processes have shortcomings in that there is a need to isolate and purify intermediate materials such as the halo ethyl sulfone compound. It would be useful to employ a process that includes minimizing human exposure to the biologically reactive halo ethyl sulfone compounds, significantly reducing the complexities of making the desired vinyl sulfone material, and significantly reducing the overall waste generation associated with the manufacture of these materials.

It is a problem to be solved to provide a process that avoids the need to isolate and purify a halo ethyl sulfone compound.

SUMMARY OF THE INVENTION

The invention provides a process comprising reacting a multi (primary alcohol sulfone) with a reducing agent and a halogenating agent in the presence of an amide compound present in an amount of less than 1 part amide per part of multi (primary alcohol sulfone) to form a multi (primary halosulfone).

The invention process avoids the need to isolate and purify a halo ethyl sulfone compound.

DETAILED DESCRIPTION OF THE INVENTION

The invention is generally summarized above.

The multi (primary alcohol sulfone) is represented by the following formula (I):

$$(HO-CH_2CH_2SO_2)_n-Z \qquad (I)$$

Z is an organic radical having a valence of n where n is 2–6. Z is preferably —A—, —O—A—O—, or —D—. A is an alkylene group containing 1 to 8 carbon atoms which may be substituted or unsubstituted, branched or unbranched and the alkylene chain may be interrupted by one or more hetero atoms or organic groups, or an arylene group which may be substituted or unsubstituted. D is a trivalent alkylene group or a trivalent arylene group that may be substituted with one or more $CH_2=CH-SO_2$-groups, or a trivalent heterocyclic group which may be substituted with one or more $CH_2=CH-SO_2$-groups. Preferred substituents for A include —OH, phenyl, aralkyl, such as phenethyl, or $CH_2=CH-SO_2$-groups. The aryl moiety of the aralkyl group may be sulfonated. The alkylene group may be interrupted by one or more of the following: oxygen atoms, arylene groups, cycloalkyl groups, —NHCONH—, or —N—R, where R is an alkyl group containing 1 to 8 carbon atoms. More preferred substituents for A include methylene and substituted alkyl groups. "n" is typically 2 and represents the preferred use of bis compounds.

The halogenating agent can be any organic or inorganic reagent suitable for displacement of primary alcohol groups and substitution with halogen atom. Preferably the halogenating agent is thionyl bromide or thionyl chloride. More preferably the halogenation reagent is a chlorinating reagent such as thionyl chloride.

Any suitable reducing agent can be used, most conveniently a reagent such as thionyl chloride can function as both a halogenating and reducing agent.

The amide compound may be represented by the following formula (II):

$$R-CO-N(R')(R'') \qquad (II)$$

wherein R, R', and R" groups can be branched, unbranched or cyclic alkyl groups or substituted or unsubstituted aryl groups with or without further functionality or heteroatoms. Preferably R is a branched or unbranched alkyl group, aromatic group, or hydrogen, typically hydrogen or a methyl or aromatic group. R' and R" are branched or unbranched alkyl groups or an aryl group and usually alkyl groups.

The amount of amide present for the transformation can be less than 1.0 part amide per part of the multi-alcoholsulfone. Preferably the amide is present at less than 0.5 part amide per part of the multi-alcoholsulfone. More preferably the amide is present at 0.1 to 0.4 parts of amide per part of the multi-alcoholsulfone.

Suitable solvents are those that don't appreciably react with the halogenating reagents such as toluene, heptane, hexane, ethyl acetate, propyl acetate, diethyl ether, isopropyl ether, dimethyl sulfoxide, methylene chloride, chloroform, carbon tetrachloride, 1,2-dichloroethane, 1,2-dimethoxyethane can be utilized. Preferably the solvent for the halogenation reaction is a solvent such as heptane, toluene, ethyl acetate, diethyl ether, methylene chloride, or hexane. More preferably the solvent is ethyl acetate, heptane, toluene or any combination of these solvents.

The reaction time is dependant on the choice of amide catalyst, halogenating reagent, temperature of the reaction and the method for neutralizing or otherwise utilizing the byproduct gasses produced in the reaction. Preferably the reaction time is 2–20 hours. Most preferred, the reaction time is 4–10 hours. The desired reaction temperature is between 45 and 80 C.

The process of the invention may comprise the further subsequent step (Stage 2) of converting the (primary halosulfone) into a (vinylsulfone) by contact with a combination of acetone, alkali metal acetate, and alkali metal bicarbonate in the presence of water. The reaction of the multi (primary halosulfone) produces a vinylsulfone compound with the following generalized formula, $(CH_2=CH-SO_2)_n-Z$, where Z will be the substitution described for the multi (primary alcohol)sulfone above. Examples of suitable vinylsulfone groups are shown in EP 0 640 589. Suitable solvents for this step include nonreactive solvents such as that used in the first step, or ethyl acetate, propyl acetate, acetone, methylethyl ketone, heptane, hexane, diethyl ether, diisopropyl ether, THF, methylene chloride, toluene, amide-containing solvents such as DMF or DMAc, DMSO or water. Preferably the solvent is heptane, ethyl acetate, acetone or a combination of these. The most preferred solvents are acetone, heptane, ethyl acetate, amide containing solvent such as DMF or DMAc with a small amount of water.

The base choice used to effect this transformation partly depends on minimizing further reaction of the base-sensitive bis(vinylsulfone) compound. The suitable bases include triethylamine and other organic amine bases, alkali metal carbonates, bicarbonates, formates, acetates, or propionates. The preferred base is a combination of alkali metal carbonates, bicarbonates, formates, acetates, or propionates. The most preferred conditions utilize a combination of alkali metal bicarbonate, and acetate in an approximate molar ratio of 3–4:1. The overall base amount is optimized to completely neutralize any residual acid present from the first stage as well as effect the elimination reaction. The base ratio is optimized in order to maximize the yield of the desired material and minimize the side-reaction products that arise from self reaction or reaction with the base or its' conjugate acid such as acetic acid.

The process of the invention may also comprise the preceding step of extraction of the multi (primary alcohol sulfone) from an aqueous reaction mixture. Solvents suitable for this process are water immiscible or partially water miscible such as toluene, C4–C6 alcohols, methyl ethyl ketone (MEK), heptane, propyl acetate or ethyl acetate. More preferably the solvent for extraction is a slightly polar solvent and has a relatively low boiling point such as butanol, MEK, propyl acetate or ethyl acetate. Most preferable, the solvent has limited solubility with water and a greater concentration of the water in its azeotrope than the solubility of water in that solvent such as butanol, propyl acetate or ethyl acetate.

Unless otherwise specifically stated, use of the term "substituted" or "substituent" means any group or atom other than hydrogen. Additionally, when the term "group" is used, it means that when a substituent group contains a substitutable hydrogen, it is also intended to encompass not only the substituent's unsubstituted form, but also its form further substituted with any substituent group or groups as herein mentioned, so long as the substituent does not destroy properties necessary for photographic utility. Suitably, a substituent group may be halogen or may be bonded to the remainder of the molecule by an atom of carbon, silicon, oxygen, nitrogen, phosphorous, or sulfur. The substituent may be, for example, halogen, such as chlorine, bromine or fluorine; nitro; hydroxyl; cyano; carboxyl; or groups which may be further substituted, such as alkyl, including straight or branched chain or cyclic alkyl, such as methyl, trifluoromethyl, ethyl, t-butyl, 3-(2,4-di-t-pentylphenoxy)propyl, and tetradecyl; alkenyl, such as ethylene, 2-butene; alkoxy, such as methoxy, ethoxy, propoxy, butoxy, 2-methoxyethoxy, sec-butoxy, hexyloxy, 2-ethylhexyloxy, tetradecyloxy, 2-(2,4-di-t-pentylphenoxy)ethoxy, and 2-dodecyloxyethoxy; aryl such as phenyl, 4-t-butylphenyl, 2,4,6-trimethylphenyl, naphthyl; aryloxy, such as phenoxy, 2-methylphenoxy, alpha- or beta-naphthyloxy, and 4-tolyloxy; carbonamido, such as acetamido, benzamido, butyramido, tetradecanamido, alpha-(2,4-di-t-pentylphenoxy)acetamido, alpha-(2,4-di-t-pentylphenoxy)butyramido, alpha-(3-pentadecylphenoxy)-hexanamido, alpha-(4-hydroxy-3-t-butylphenoxy)tetradecanamido, 2-oxo-pyrrolidin-1-yl, 2-oxo-5-tetradecylpyrrolin-1-yl, N-methyltetradecanamido, N-succinimido, N-phthalimido, 2,5-dioxo-1-oxazolidinyl, 3-dodecyl-2,5-dioxo-1-imidazolyl, and N-acetyl-N-dodecylamino, ethoxycarbonylamino, phenoxycarbonylamino, benzyloxycarbonylamino, hexadecyloxycarbonylamino, 2,4-di-t-butylphenoxycarbonylamino, phenylcarbonylamino, 2,5-(di-t-pentylphenyl)carbonylamino, p-dodecylphenylcarbonylamino, p-tolylcarbonylamino, N-methylureido, N,N-dimethylureido, N-methyl-N-dodecylureido, N-hexadecylureido, N,N-dioctadecylureido, N,N-dioctyl-N'-ethylureido, N-phenylureido, N,N-diphenylureido, N-phenyl-N-p-tolylureido, N-(m-hexadecylphenyl)ureido, N,N-(2,5-di-t-pentylphenyl)-N'-ethylureido, and t-butylcarbonamido; sulfonamido, such as methylsulfonamido, benzenesulfonamido, p-tolylsulfonamido, p-dodecylbenzenesulfonamido, N-methyltetradecylsulfonamido, N,N-dipropylsulfamoylamino, and hexadecylsulfonamido; sulfamoyl, such as N-methylsulfamoyl, N-ethylsulfamoyl, N,N-dipropylsulfamoyl, N-hexadecylsulfamoyl, N,N-dimethylsulfamoyl; N-[3-(dodecyloxy)propyl]sulfamoyl, N-[4-(2,4-di-t-pentylphenoxy)butyl]sulfamoyl, N-methyl-N-tetradecylsulfamoyl, and N-dodecylsulfamoyl; carbamoyl, such as N-methylcarbamoyl, N,N-dibutylcarbamoyl, N-octadecylcarbamoyl, N-[4-(2,4-di-t-pentylphenoxy)butyl]carbamoyl, N-methyl-N-tetradecylcarbamoyl, and N,N-dioctylcarbamoyl; acyl, such as acetyl, (2,4-di-t-amylphenoxy) acetyl, phenoxycarbonyl, p-dodecyloxyphenoxycarbonyl methoxycarbonyl, butoxycarbonyl, tetradecyloxycarbonyl, ethoxycarbonyl, benzyloxycarbonyl, 3-pentadecyloxycarbonyl, and dodecyloxycarbonyl; sulfonyl, such as methoxysulfonyl, octyloxysulfonyl, tetradecyloxysulfonyl, 2-ethylhexyloxysulfonyl, phenoxysulfonyl, 2,4-di-t-pentylphenoxysulfonyl, methylsulfonyl, octylsulfonyl, 2-ethylhexylsulfonyl, dodecylsulfonyl, hexadecylsulfonyl, phenylsulfonyl, 4-nonylphenylsulfonyl, and p-tolylsulfonyl; sulfonyloxy, such as dodecylsulfonyloxy, and hexadecylsulfonyloxy; sulfinyl, such as methylsulfinyl, octylsulfinyl, 2-ethylhexylsulfinyl, dodecylsulfinyl, hexadecylsulfinyl, phenylsulfinyl, 4-nonylphenylsulfinyl, and p-tolylsulfinyl; thio, such as ethylthio, octylthio, benzylthio, tetradecylthio, 2-(2,4-di-t-pentylphenoxy)ethylthio, phenylthio, 2-butoxy-5-t-octylphenylthio, and p-tolylthio; acyloxy, such as acetyloxy, benzoyloxy, octadecanoyloxy, p-dodecylamidobenzoyloxy, N-phenylcarbamoyloxy, N-ethylcarbamoyloxy, and cyclohexylcarbonyloxy; amine, such as phenylanilino, 2-chloroanilino, diethylamine, dodecylamine; imino, such as 1 (N-phenylimido)ethyl, N-succinimido or 3-benzylhydantoinyl; phosphate, such as dimethylphosphate and ethylbutylphosphate; phosphite, such as diethyl and dihexylphosphite; a heterocyclic group, a heterocyclic oxy group or a heterocyclic thio group, each of which may be substituted and which contain a 3 to 7 membered heterocyclic ring composed of carbon atoms and at least one hetero atom selected from the group consisting of oxygen, nitrogen and sulfur, such as 2-furyl, 2-thienyl, 2-benzimidazolyloxy or 2-benzothiazolyl; quaternary ammonium, such as triethylammonium; and silyloxy, such as trimethylsilyloxy.

If desired, the substituents may themselves be further substituted one or more times with the described substituent groups. The particular substituents used may be selected by those skilled in the art to attain the desired photographic properties for a specific application and can include, for example, hydrophobic groups, solubilizing groups, blocking groups, releasing or releasable groups, etc. When a molecule may have two or more substituents, the substituents may be joined together to form a ring such as a fused ring unless otherwise provided. Generally, the above groups and substituents thereof may include those having up to 48 carbon atoms, typically 1 to 36 carbon atoms and usually less than 24 carbon atoms, but greater numbers are possible depending on the particular substituents selected.

The starting material may be purchased or made, for example, as follows. Bis(2-hydroxyethylsulfonyl)methane is formed by aqueous hydrogen peroxide oxidation of 3,5-dithiaheptane-1,7-diol. After the oxidation reaction is complete to form theoretically 55.23 grams (0.238 mol) of bis(2-hydroxyethylsulfonyl)methane), the excess hydrogen peroxide is destroyed by addition of 2.08 grams sodium bisulfite. Following 30 minutes of stirring at 70° C., 66 ml of water are vacuum distilled from the reaction mixture to provide an approximately 60 wt % bis(2-hydroxyethylsulfonyl)methane) solution for the extraction isolation process. This remaining 68 ml of product, water, impurities and various salts, are transferred to a 250 ml 2-neck flask equipped with a dip tube and magnetic stir bar. The dip tube must be the correct length and essentially reach the bottom of the flask. A 4-neck 500 ml distillation flask is positioned by the extraction receiver flask and equipped with a glass condenser such that the condensate will flow through the dip tube. The second neck of the extraction flask is connected with tubing to one of the available necks of the distillation flask. Elevations must be considered to prevent flooding of the condenser and proper flow of the ethyl acetate through the apparatus. Ethyl acetate is added to the extraction flask on top of the product concentrate. Add sufficient ethyl acetate to completely fill the extraction flask. To the distillation flask, add 250 ml of ethyl acetate. Heat the ethyl acetate to 40–45° C. while pulling vacuum on the entire system via the connection at the top of the condenser to distill the ethyl acetate. Control the vacuum level to 225–250 torr as required. Gently stir the product layer in the extraction flask using the magnetic stir bar. Continue this extraction of the product for 6–8 hours. During this time, product will begin to crystallize out of the ethyl acetate in the distillation flask and the volume of the product/water layer in the extraction flask will decrease. After the 6–8 hours of extraction, stop the operation and remove all the ethyl acetate from the distillation flask containing the product by evaporation. Typical yields are 90–95% and assays by GC are 97.5–99.5% bis(2-hydroxyethylsulfonyl)methane). Levels of Na and Ca in the product are typically less than 20 ppm.

EXAMPLE 1

Stage 1

A slurry of 120 g (0.517 mol) bis(2-hydroxyethylsulfonyl)methane, 54.7 g heptane and 7.0 g (0.08 mol) dimethylacetamide is heated to 72 C. and 120 g (1.01 mol) thionyl chloride is added in a slow dropwise manner over about 4 hours. To the reaction mixture is added 72 g of ethyl acetate and then an additional 14.2 g (0.119 mol) thionyl chloride is added in a dropwise manner to complete the chlorination as determined by nmr spectroscopy. The reaction mixture is allowed to degas for 30 min, then vacuum is applied and the residual gas and solvents are reduced by distillation. To the reaction mixture is added 100 ml of acetone, vacuum is applied and the solvent is distilled to remove the remaining solvents from the bis(2-chloroethylsulfonyl)methane.

Stage 2

A slurry of the bis(2-chloroethylsulfonyl)methane is prepared by adding 90 g of acetone to the above reaction mixture and warming to 26 C. To the slurry is added 0.2 g (0.94 mmol) 3,5-dinitro-benzoic acid, 19.3 g (0.235 mol) sodium acetate, 7 g of water and 74.4 g (0.886 mol) sodium bicarbonate. The slurry is stirred for 5–6 hours until the in-process LC monitoring shows the reaction is complete. To the reaction mixture is added 6 g (0.163 mol) concentrated hydrochloric acid. The mixture is filtered to remove salts and to the filtrate is added 2.2 g (10.4 mmol) 3,5-dinitro-benzoic acid. The solution is concentrated to an oil under vacuum. The oil is crystallized from a mixture of 39.3 g of methanol and 124 g of isopropanol to give 83.6 g (82%) of bis(vinylsulfonyl)methane meeting all quality specifications.

EXAMPLE 2

Stage 1

The reaction is run as above using the same conditions except 7.0 g (0.096 mol) dimethylformamide is substituted for the dimethylacetamide.

Stage 2

Using the same reaction conditions as in example 1, 84.5 g (83%) of bis(vinylsulfonyl)methane is produced meeting all quality specifications.

The entire contents of the patents and other publications referred to in this specification are incorporated herein by reference.

What is claimed is:

1. A process comprising reacting an alcohol-sulfone compound represented by the formula:

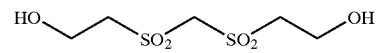

with a reducing agent and a halogenating agent in the presence of a solvent that does not appreciably react with the halogenating agent and in the presence of an amide compound present in an amount of less than 1 part amide per part of alcohol sulfone to form a halosulfone, wherein the amide compound is represented by the following formula (II):

wherein R, R', and R" groups are branched, unbranched or cyclic alkyl groups or substituted or unsubstituted aryl groups;

and then, without isolating the halosulfone, converting the halosulfone into a vinylsulfone by contact with a base selected from the alkali metal carbonates, bicarbonates, formates, acetates, and propionates in the presence of a solvent and water.

2. The process of claim 1 wherein the halogenating agent is a chlorinating or brominating agent.

3. The process of claim 1 wherein the halogenating agent is thionyl bromide or thionyl chloride.

4. The process of claim 1 wherein the halogenating agent is thionyl chloride.

5. The process of claim 1 wherein R is a branched or unbranched alkyl group, aromatic group, or hydrogen.

6. The process of claim 1 wherein R is hydrogen, methyl or an aromatic group.

7. The process of claim 1 wherein R' and R" are branched or unbranched alkyl groups or an aryl group.

8. The process of claim 1 wherein the amide is present in an amount less than 1.0 part amide per part of the alcohol-sulfone.

9. The process of claim 1 wherein the amide is present in an amount less than 0.5 parts amide per part of the alcohol-sulfone.

10. The process of claim 1 wherein the amide is present in an amount 0.1 to 0.4 parts amide per part of the alcohol-sulfone.

11. The process of claim 1 wherein the solvent in the halosulfone forming step is one that doesn't appreciably react with the halogenating reagents.

12. The process of claim 1 wherein the solvent in the converting step is selected from acetone, heptane, ethyl acetate and an amide containing solvent.

13. The process of claim 1 including the preliminary step of extracting the alcohol sulfone from an aqueous reaction mixture.

* * * * *